United States Patent
Varnes

Patent Number: 5,261,816
Date of Patent: Nov. 16, 1993

[54] DENTAL HANDPIECE COOLANT DELIVERY SYSTEM

[76] Inventor: DeWayne L. Varnes, R.R. 1, Ridgeland, Wis. 54763

[21] Appl. No.: 35,842

[22] Filed: Mar. 23, 1993

[51] Int. Cl.⁵ .............................................. A61C 1/10
[52] U.S. Cl. .................................. 433/84; 433/82; 433/98
[58] Field of Search ................... 433/82, 84, 85, 98

[56] References Cited

U.S. PATENT DOCUMENTS

| | | | |
|---|---|---|---|
| 3,505,737 | 4/1970 | Merolla | 433/82 |
| 3,638,310 | 2/1972 | Austin, Jr. | 433/98 |
| 4,302,185 | 11/1981 | Hall | 433/84 |
| 4,470,812 | 9/1984 | Martens et al. | 433/85 |
| 4,973,247 | 11/1990 | Varnes et al. | 433/85 |

*Primary Examiner*—John J. Wilson
*Attorney, Agent, or Firm*—Haugen and Nikolai

[57] ABSTRACT

A coolant delivery system for a high speed dental cutting handpiece. The system includes a coolant reservoir, a selectively operable pressurized gas source, and a pressurized-gas distribution structure. The distribution structure has a gas entry chamber, a first passage having a reduced cross-section dimension leading from the entry chamber to the reservoir, a second passage leading from the reservoir to the entry chamber, and a third passage leading from the entry chamber to the exterior. Within the entry chamber is disposed a closure member, preferably a flexible membrane, which is situated to close the second and third passages when pressurized gas, en route from the gas source to the first passage for pressurization of the reservoir and ultimate coolant delivery to the handpiece, strikes the closure member. Coolant flow from the reservoir begins substantially coincidentally with handpiece operation and ceases substantially immediately with cessation of handpiece operation since pressurizing gas can then escape from the reservoir through the second and third passages.

8 Claims, 2 Drawing Sheets

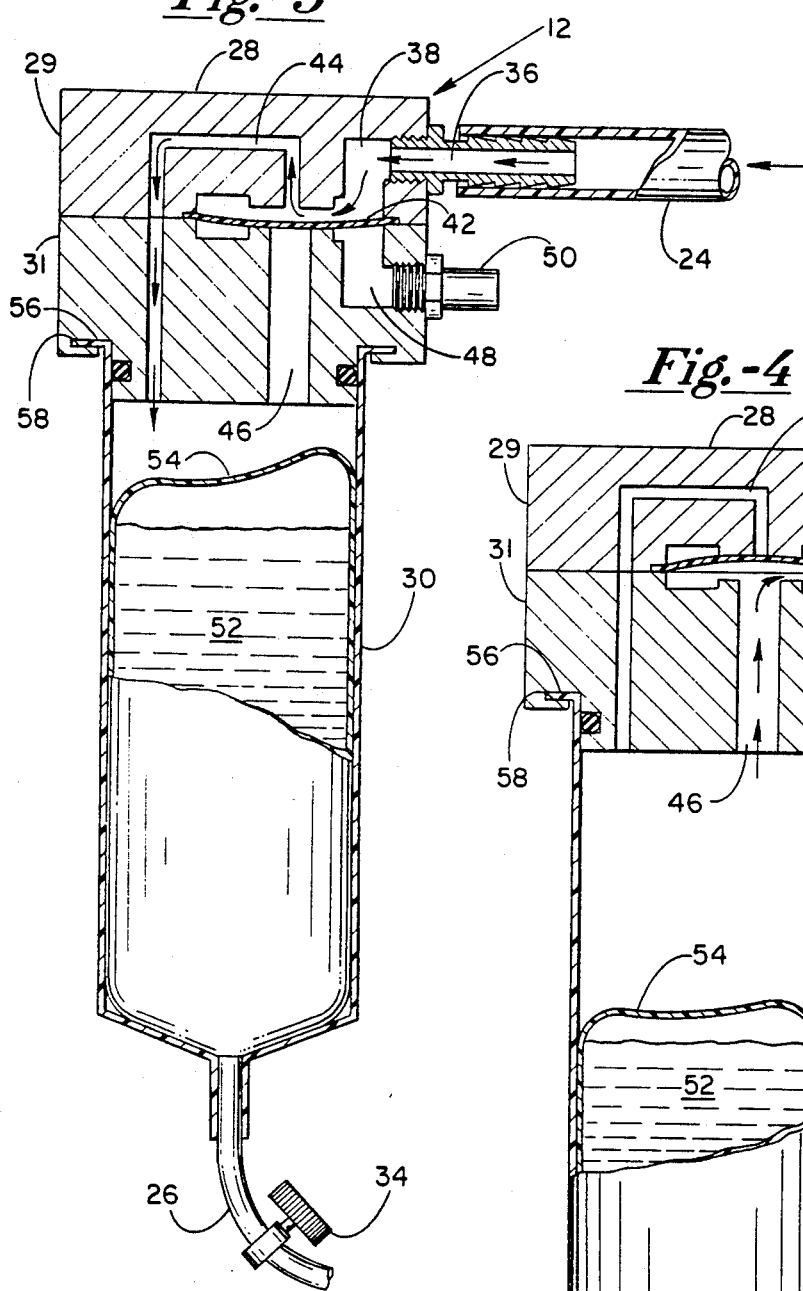
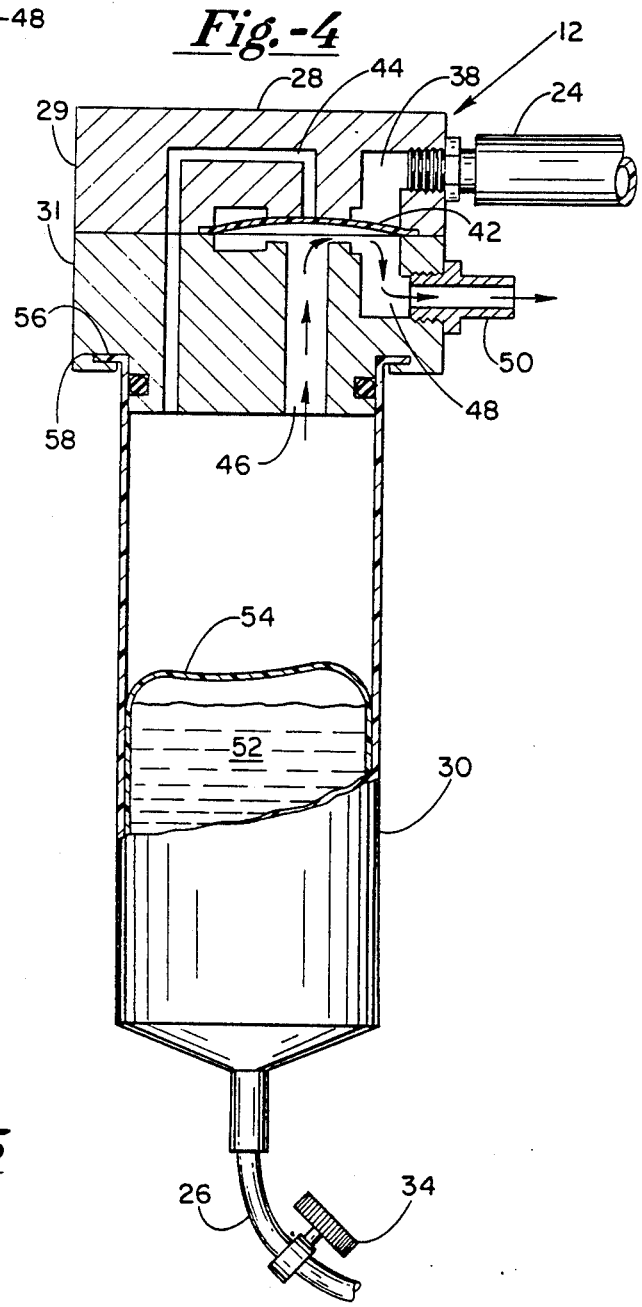
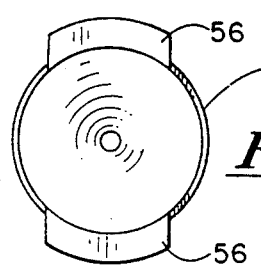

DENTAL HANDPIECE COOLANT DELIVERY SYSTEM

BACKGROUND OF THE INVENTION

Field of the Invention

This invention relates in general to a coolant delivery system for a high speed dental cutting handpiece, and in particular to a coolant delivery system wherein coolant delivery ceases substantially immediately with cessation of handpiece cutting action.

The use of high speed dental handpieces such as drills employed in preparing teeth for fillings and the like requires that this equipment be kept at a reasonable temperature while in the mouth of a patient. Because of the high speed of a drill, for instance, heat generated by friction as the drill contacts a tooth could easily burn tissue in the mouth. To alleviate this problem, handpieces usually have a coolant spray or mist, which is generally water, that encompasses the work area and is emitted from the distal end of the handpiece.

One problem which can occur in such an apparatus is that of backflow of saliva, blood and the like from the mouth of the patient into the reservoir which houses the coolant. As described in U.S. Pat. Nos. 4,470,812 and 4,973,247, incorporated herein by reference, such an event can result in contamination of the coolant and subsequent transfer of these untoward materials to other patients. As taught in these two patents, disposable or sterilizable reservoir containers can aid in the prevention of this condition. A second problem which can occur is that of excess coolant flow after a handpiece is deactivated. Such a condition results in a poor work field, inconvenience for the dentist, and discomfort for the patient.

It is therefore a primary object of the present invention to provide a coolant delivery system wherein coolant delivery occurs substantially only when the handpiece is operational.

Another object of the present invention is to provide a coolant delivery system wherein gas pressure which operates a dental handpiece also operates simultaneous coolant delivery.

These and other objects of the present invention will become apparent throughout the description which now follows.

SUMMARY OF THE INVENTION

The present invention is a coolant delivery system for a high speed dental cutting handpiece. In addition to including a reservoir for housing a coolant and a selectively operable pressurized-gas source, the system includes a pressurized-gas distribution structure comprising a pressurized-gas entry chamber and a first passage leading from the entry chamber to the reservoir. A second passage leads from the reservoir back to the entry chamber. Within the entry chamber is disposed a closure member which is situated to close the second passage when pressurized gas en route from the pressurized-gas source to the first passage strikes the closure member. A third passage leads from the entry chamber to the exterior of the system and is situated such that the closure member when closed also closes access to this third passage. Finally, a coolant delivery conduit such as a flexible tube leads from the reservoir to the handpiece for delivery of coolant at the distal end of the handpiece. The pressurized-gas source is selectively operable as with a foot pedal, for example, and preferably has a single gas delivery conduit which has a first delivery branch terminating in the handpiece to thereby drive the handpiece when gas is flowing through the conduit and a second delivery branch in communication with the gas distribution structure. Preferably, the closure member is a flexible membrane mounted within the entry chamber and displaceable by gas pressure impinging thereon to thereby close the passage leading from the coolant storage portion as well as the passage leading to the exterior of the system. In operation, pressurized gas simultaneously operates the handpiece and enters the gas distribution structure to thereby pressurize the reservoir by closing the second and third passage in the distribution structure. Because of reservoir pressurization, coolant is forced to flow to the handpiece. Upon cessation of pressurized gas delivery, the handpiece stops, and, simultaneously, the closure member in the gas distribution structure opens to thereby open second passage to permit residual pressurized gas to escape through the second passage into the entry chamber and out through the third passage to the exterior of the system.

BRIEF DESCRIPTION OF THE DRAWINGS

FIG. 3 is a side elevation view in section of the apparatus of FIG. 2 in operation;

FIG. 4 is a side elevation view in section of the apparatus of FIG. 2 immediately upon cessation of operation;

FIG. 5 is a top plan view of the coolant reservoir.

DETAILED DESCRIPTION OF A PREFERRED EMBODIMENT

Figure 1:
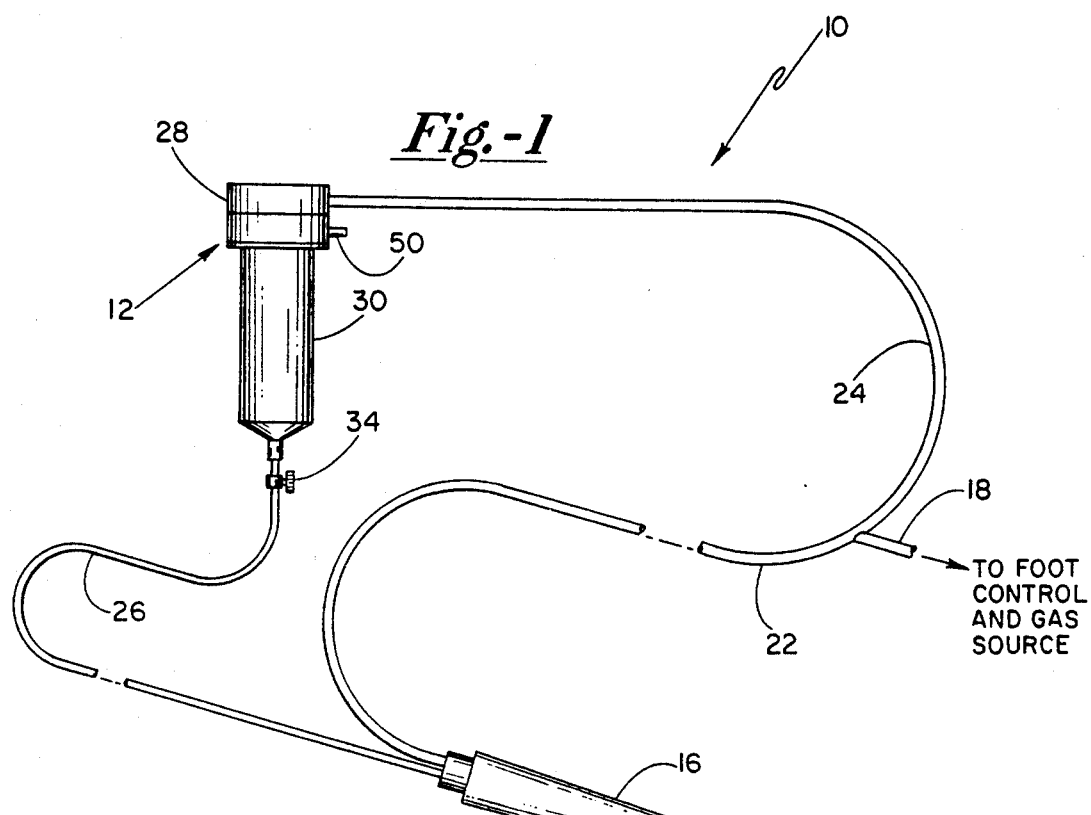
FIG. 1 is a side elevation view of a dental handpiece drive system incorporating a coolant delivery system.
Figure 2:
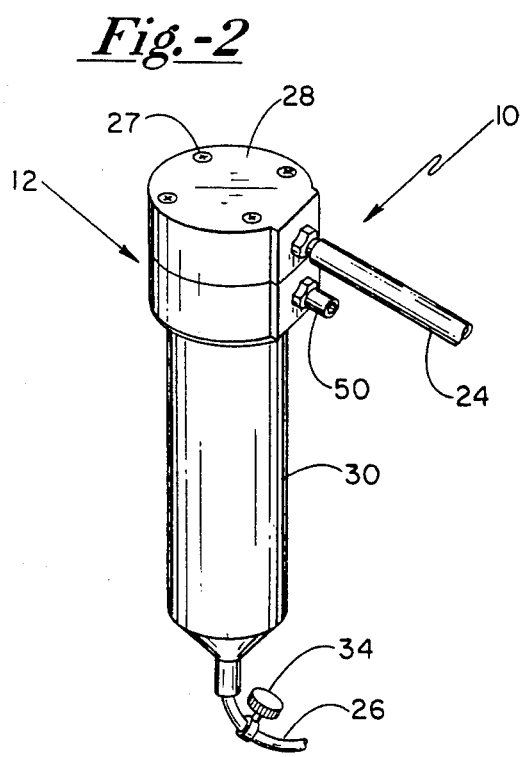
FIG. 2 is a perspective view of a portion of the coolant delivery system of FIG. 1 and illustrating the exterior of a pressurized-gas distribution structure and coolant reservoir.

Referring to FIGS. 1 and 2, a dental handpiece drive system 10 is illustrated and includes a coolant delivery system 12 disposed between a conventional pressurized-gas (air) source (not shown) and a handpiece 16 and is operated by a conventional, selectively-operable, closable valve activated by a foot pedal (not shown) as known in the art. The pressurized-gas line 18 has two branches 22, 24, with the first branch 22 thereof leading directly to the handpiece 16 to thereby operate a conventional turbine drive in the handpiece as known in the art within the handpiece 16. The second branch 24 of the pressurized-gas line 18 leads to the coolant delivery system 12 for pressurization of coolant therein and ultimate delivery therefrom through a conduit 26 to the handpiece 16. The coolant delivery system 12 includes a pressurized-gas distribution structure 28 and a removable reservoir 30 where coolant is housed. Desired coolant flow volume from the reservoir 30 can be regulated by a conventional hand-operable screw clamp closure 34, as known in the art, placed on the conduit 26. Coolant flow volume is usually calibrated by the dentist who sets the screw clamp closure 34 for desired coolant flow at maximum turbine drive magnitude. In this manner, flow volume is reduced at lower turbine speed and increases to maximum flow velocity when the turbine drive is operated at full speed. The coolant delivery system 12 can be mounted to a stand, work table or the like for convenient placement near a patient.

FIGS. 3 and 4 show the pressurized-gas distribution structure 28 and reservoir 30 in section. The structure 28 is constructed of an upper piece 29 and a lower piece 31 secured to each other by conventional screws 27 as seen in FIG. 2. An entry port 36 accepts the second branch 24 of the pressurized-gas line 18 and permits gas entry into a pressurized-gas entry chamber 38 when the foot pedal is activated by the dentist. The structure 28 is provided with a first passage 44 leading from the chamber 38 to the reservoir 30; a second passage 46 leading from the reservoir 30 back to the chamber 38; and a third passage 48 leading to the exterior via an exit port 50. The cross-section dimension (diameter) of the first passage 44 is here shown at about one-third the cross-section dimension of the entry chamber 38 so that a Venturi effect occurs to thereby increase gas pressure entering the reservoir 30. The cross-section dimension of the first passage 44 should be no greater than about 50%, preferably between 25% and 50%, of the diameter of the entry chamber 38 so that gas entering the reservoir 30 is adequately pressurized. The cross-section dimension of the second passage 46 is larger than that of the first passage 44. A flexible circular membrane 42, preferably constructed of silicone rubber and secured in place at its border between the upper piece 29 and lower piece 31 of the structure 28, overlays the openings of the second and third passages 46, 48 in the chamber 38. While the reservoir 30 can directly house coolant, it is preferable that coolant 52 be disposed within a flexible and collapsible bladder 54 from which the conduit 26 extends. It is most preferable that the bladder 54 and conduit 26 be disposable, be of one-piece construction, and be provided to the dentist with coolant 52 in place therein. The dentist then conveniently removes the reservoir 30 from the structure 28 and places the bladder 54 within the reservoir 30 after guiding the conduit 2 out the bottom of the reservoir 30. Thereafter, the reservoir is once again secured to the gas distribution structure 28 and the coolant 52 within the bladder 54 has not been subjected to possible contamination. The amount of coolant is preferably from about 30 to 50 ml. Attachment of the reservoir 30 to the gas distribution structure 28 can be by any suitable means as would be recognized in the art to achieve an air-tight fit. In the preferred embodiment, the reservoir 30 is constructed as a conventional syringe body having opposing laterally-extending flanges 56 which fit within laterally opposing complimentary horizontal retainer grooves 58 at the base of the gas distribution structure 28. The reservoir 30 is thereafter positioned so that a quarter-turn rotation of the reservoir 30 locks the reservoir in place.

In operation, when pressurized gas enters the chamber 38 via the entry port 36, it is immediately diverted downwardly as illustrated by the arrows in FIG. 3 to strike the top surface of the flexible membrane 42 to force the membrane 42 against the openings of the second and third passages 46, 48 and thereby close these passages. The gas flows through the first passage 44 into the reservoir 30 where it pressurizes the reservoir for resultant coolant exit into and through the conduit 26 and delivery to the handpiece 16. Because the second and third passages 46, 48 are blocked by the membrane 42 while gas is flowing, the reservoir is maintained in a pressurized state.

As earlier discussed, it is important that coolant flow to the handpiece ceases when handpiece activation ceases. The pressurized-gas distribution structure 28 accomplishes such flow cessation substantially immediately with the cessation of pressurized gas delivery. In particular, when pressurized gas is discontinued by deactivation of the foot pedal 20, gas entering the entry port 36 immediately stops. Likewise, and as illustrated in FIG. 4, force from flowing gas against the top surface 40 of the membrane 42 also stops, resulting in the opening of the second and third passages 46, 48. Residual gas within the reservoir 30, instead of causing more coolant to be discharged, forces the membrane 42 upwardly as shown by the arrows in FIG. 4 and travels through the now-open second and third passages 46, 48 for external dissipation through the exit port 50. In this manner coolant flow and handpiece operation becomes substantially coincidental.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

I claim:

1. A coolant delivery system for a high speed dental cutting handpiece, the system comprising:
   (a) a reservoir for housing a coolant;
   (b) a selectively operable pressurized gas source having a first ga delivery branch terminating in the handpiece to drive the handpiece when gas is flowing through the first gas delivery branch, and a second gas delivery branch;
   (c) a pressurized gas distribution structure comprising:
     (i) a pressurized-gas entry chamber in communication with the second gas delivery branch;
     (ii) a first passage leading from the entry chamber to the reservoir, said first passage having a cross-section dimension between about 25% and about 50% of the cross-section dimension of the entry chamber;
     (iii) a second passage leading from the reservoir to the entry chamber, said second passage having a cross-section diameter larger that the cross-section diameter of the first passage;
     (iv) a closure member disposed within the entry chamber and situated to close the second passage when pressurized gas from the terminal end of the first gas delivery branch en route to the first passage strikes the closure member;
     (v) a third passage leading from the entry chamber to the exterior of the system and situated such that the closure member when closed also closes access to the third passage; and
   (d) a coolant delivery conduit leading from the reservoir to the handpiece.

2. A coolant delivery system as claimed in claim 1 wherein the first and second delivery branches of the pressurized gas source originate from a single conduit leading from the pressurized gas source.

3. A coolant delivery system as claimed in claim 2 wherein the closure member is a flexible membrane.

4. A coolant delivery system as claimed in claim 1 wherein the closure membrane is a flexible membrane.

5. A coolant delivery system for a high speed dental cutting handpiece, the system comprising:
   (a) a reservoir for housing a coolant, said coolant being disposed in a flexible and collapsible bladder;
   (b) a selectively operable pressurized gas source having a first gas delivery branch terminating in the handpiece to drive the handpiece when gas is flowing through the first gas delivery branch, and a second gas delivery branch;
(c) a pressurized gas distribution structure comprising:
  (i) a pressurized-gas entry chamber in communication with the second gas delivery branch;
  (ii) a first passage leading from the entry chamber to the reservoir, said first passage having a cross-section dimension between about 25% and about 50% of the cross-section dimension of the entry chamber;
  (iii) a second passage leading from the reservoir to the entry chamber, said second passage having a cross-section diameter larger that the cross-section diameter of the first passage;
  (iv) a closure member disposed within the entry chamber and situated to close the second passage when pressurized as from the terminal end of the first gas delivery branch en route to the first passage strikes the closure member;
  (v) a third passage leading from the entry chamber to the exterior of the system and situated such that the closure member when closed also closes access to the third passage; and
(d) a coolant delivery conduit leading from the reservoir to the handpiece.

6. A coolant delivery system as claimed in claim 5 wherein the bladder and coolant delivery conduit are of one-piece construction.

7. A coolant delivery system as claimed in claim 5 wherein the first and second delivery branches of the pressurized gas source originate from a single conduit leading from the pressurized gas source.

8. A coolant delivery system as claimed in claim 5 wherein the closure member is a flexible membrane.

* * * * *